United States Patent [19]

Schiller et al.

[11] Patent Number: 4,787,742

[45] Date of Patent: Nov. 29, 1988

[54] DIRECT FINGER READING

[75] Inventors: Michael Schiller, Riverdale; Daniel H. Marcus, New City, both of N.Y.

[73] Assignee: Fingermatrix, Inc., North White Plains, N.Y.

[21] Appl. No.: 8,590

[22] Filed: Jan. 29, 1987

Related U.S. Application Data

[63] Continuation-in-part of Ser. No. 630,012, Jul. 12, 1984.

[51] Int. Cl.$^4$ .............................................. G06K 9/20
[52] U.S. Cl. ...................................................... 356/71
[58] Field of Search ........................ 356/71; 382/4, 5; 340/825.34

[56] References Cited

U.S. PATENT DOCUMENTS

| | | | |
|---|---|---|---|
| 3,614,737 | 10/1971 | Sadowski | 340/146.3 |
| 3,716,301 | 2/1973 | Caulfield et al. | 356/71 |
| 4,322,163 | 3/1982 | Schiller | 356/71 |
| 4,385,831 | 5/1983 | Ruell | 356/71 |
| 4,428,670 | 1/1984 | Ruell et al. | 356/71 |
| 4,553,837 | 11/1985 | Marcus | 356/71 |

FOREIGN PATENT DOCUMENTS 1090475  11/1980  Canada .

*Primary Examiner*—R. A. Rosenberger
*Attorney, Agent, or Firm*—McAulay, Fields, Fisher, Goldstein & Nissen

[57] ABSTRACT

The technique for optically scanning a finger to produce a fingerprint image involves positioning the finger surface to be optically scanned so that it is exposed and, in particular, is not pressed against a platen. A slit light beam along the length of the forward part of the finger is circumferentially rotated about an axis about the nominal center of the finger. A reflected slit light beam carries modulation information which is focused on a linear array of photo-electric transducers to provide the fingerprint image. The interrogating light is coherent, substantially collimated, light. The plane of the interrogating slit light beam and the plane of the reflected modulated slit light beam are coplanar thereby establishing an illumination plane. The illumination plane is parallel to the axis of the finger and is rotated about that axis during the interrogating scan. The illumination plane is slightly offset from that rotational axis and the incident light in the illumination plane impinges on the finger surface at a slight off-normal axis. This offset and off-normal incidence creates two dimensional shadowing. The finger surface being interrogated is positioned slightly off of the object plane for the downstream focusing optics thereby creating a constructive and destructive interference effect at the image plane defined by the transducers.

10 Claims, 1 Drawing Sheet

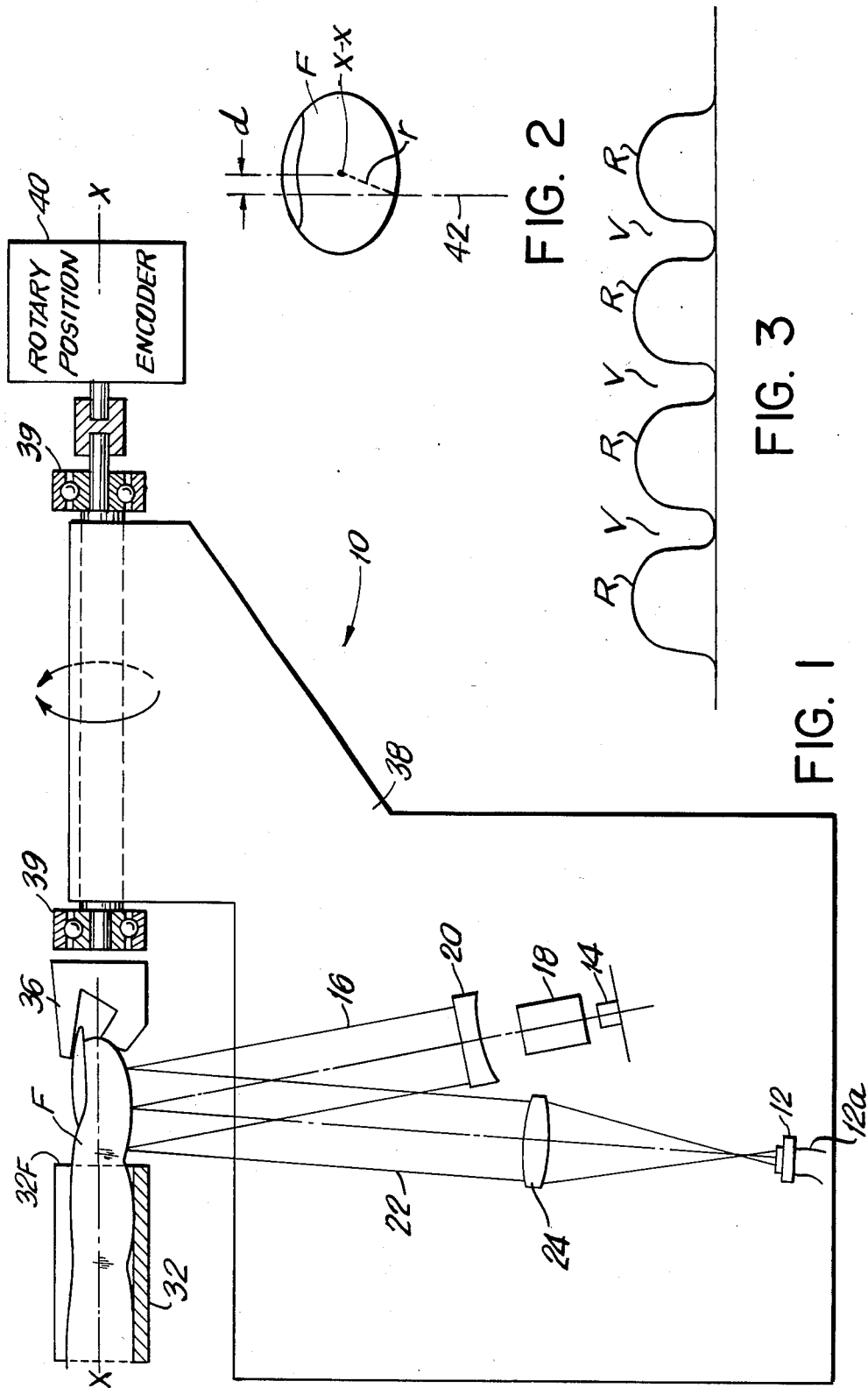

DIRECT FINGER READING

RELATED APPLICATION

This application is a continuation-in-part of patent application Ser. No. 630,012 filed on July 12, 1984 and entitled Direct Finger Reading.

BACKGROUND OF THE INVENTION

This invention relates generally to an optical finger image generating apparatus and, more importantly, to an optical finger image apparatus which generates an image from a scan of a finger object without a platen.

Fingerprint apparatus capable of generating a fingerprint image which can be encoded into machine readable signals are known in the art. Examples, of such apparatus are described in U.S. Pat. No. 4,322,163. This apparatus generates a fingerprint image using substantially collimated light as an interrogating light beam which is displaced across a platen upon which a finger is supported. The finger on the platen modulates the interrogating light beam to provide a reflected light beam which has fingerprint information. Optical scanning means are used which cause the interrogating light beam to scan the fingerprint object carried by the finger on the platen. The modulated light beam is imaged onto an array of photo-electric transducers to produce a series of output signals indicative of the modulated information. The output of the array is serially interrogated at successive scan positions to provide a set of signals containing fingerprint information.

In the art of optical finger image processing, it is desirable to keep the system as inexpensive as possible and the size of the system as small as possible while ensuring that the reliability of the system is maintained. In order to get a useful fingerprint image the background signal must be kept as low and as steady as possible. Further, there must be a high resolution image of the fingerprint object. Prior art apparatus while providing a reliable system with high resolution and a controlled background signal uses platens upon which the finger being scanned is supported. Although the platens help to control the background signal and aid in resolution they also create problems. With use, deposits of oil, grease and dirt build up on the platen which affect the fingerprint image. Further, the pressure of a finger against the platen distorts the fingerprint object and the distortion is somewhat different each time the finger is applied to the platen.

These distortions arise out of at least four types of situations. There is a tendency for the ridges to close down on the valleys in the higher frequency portions of a finger when the finger is pressed against a platen. The positioning of a finger on the platen requires movement of the finger along the platen to a pre-determined position and this generates a slip-stick distortion due to the friction of the finger on the platen surface. A third type of distortion is latent image distortion which arises from the latent images left by previous applications of a finger to a platen. A fourth type of distortion occurs because of the interaction of the finger oil with the platen. This last distortion is particularly severe with fingers which generate a great deal of oil. All these distortion situations tend to be non-repeatable so that the finger image varies as between applications of the same finger to a platen. This complicates analysis and requires relatively expensive processing to compensate for these distortions.

U.S. Pat. No. 3,614,747 to Charles Sadowsky discloses a fingerprint apparatus which uses regular light to scan a portion of a finger through a slit. The Sadowsky apparatus uses and must use a point illumination to keep the background light level (that is, the base line in the electrical signal) as low as possible. Sadowsky employs a shadowing technique to generate differential illumination of ridges and valleys by scanning an interrogating point of light along a single slit aperture.

It is an object of the present invention to provide an optical finger image processing apparatus which produces accurate fingerprint images without using a platen.

Another object of the present invention is to provide such an apparatus which avoids swamping out the image signal with the base line signal.

It is a further object to provide such an apparatus which is relatively inexpensive, reliable and provides a repeatable image.

Still a further object is to provide such an apparatus which is relatively small in size.

It is an object of this invention to meet the various objects stated above in a device that will be effective with the wide range of finger surfaces that exist in the population including fingers in which the valleys are shallow and fingers where the valleys are deep and including fingers where the ridges are quite narrow and fingers where the ridges are relatively broad.

Brief Description of the Drawings

FIG. 1 is an optical and mechanical schematic of the device of this invention showing a finger in position being interrogated by a light beam 16.

FIG. 2 is a partial illustration of the FIG. 1 apparatus looking into the tip of the finger. FIG. 2 illustrates, in exaggerated form, the offset d between the illumination plane and the axis of rotation of the optical interrogating and detecting unit.

FIG. 3 is a schematic idealized representation of the typical relationship between the ridge zones R and valley zones V of an undistorted finger.

Brief Description

In brief, the device of this invention provides for the direct reading of the surface of a finger with a coherent collimated interrogating light beam. The light beam reflected from the finger surface that is interrogated by the coherent light beam will contain fingerprint information. This reflected light beam is incident on a linear array of photo-electric transducers. Thus, at any one moment in time, only a thin line across the finger is imaged at the linear array of transducers. Accordingly, only a thin slit of the interrogating light beam is required to produce imagery at the transducer array. Thus, the interrogating light beam is shaped by cylindrical beam forming lenses into a flat planar like beam that impinges on the finger as a slit of light. The plane of the interrogating light beam and the plane of the reflected modulated light beam are co-planar. The line of interrogation is roughly parallel to the axis of the finger being interrogated.

The co-planar interrogating light beam and reflected modulated light beam form an illumination plane. This illumination plane is scanned around the finger in a circumferential direction perpendicular to the illumination plane. The optical scan involves rotation of the illumination plane so as to maintain the illumination plane parallel to a pre-determined axis, which axis is the nominal axis of an idealized cylindrical finger.

The rotation of the illumination plane around the surface of the finger provides an output image which is the equivalent to a full roll of a fingerprint in a fingerprint inking technique. Accordingly, the arc of rotation of the optical interrogating and detection unit is sufficient to provide this full roll finger image.

It is because of this rotation of the illumination plane around the surface of a finger not supported on a platen that requires the co-planarity between the interrogating light beam and the reflected modulated light beam. Since the finger surface is not a uniform cylinder, there would be substantial geometric distortion of the image at the array during the course of the scan. In order to make sure that the longitudinal line along the finger that is being interrogated appears at the linear array of transducers, it is necessary that the interrogating plane and the reflected modulated plane be the same.

A laser diode provides a coherent light beam which is shaped into a substantially collimated interrogating plane of light by an assemblage of spherical and cylindrical lenses. The interrogating light beam is scanned across the finger to interrogate that portion of the finger which extends beyond the support and to produce the reflected light beam having fingerprint information. Within the illumination plane, the collimated interrogating light beam is at an angle to a line normal to the surface of the finger being interrogated. Thus, within the illumination plane the interrogating light rays strike the surface of the finger at a slight off normal angle. In addition, the illumination plane is offset slightly from the axis of rotation so as to assure that the illumination plane is not quite perpendicular to the surface of the finger at the line of interrogation. The combination of the off-normal angle within the illumination plane and the offset of the illumination plane from the nominal axis of the finger assures that there will be shadowing in two dimensions.

The optical system, including the laser diode, the interrogating beam, the beam forming lenses, the transducer array and the focusing lens assembly which focuses an image on the transducer array are all mounted on a platform which rotates about the nominal axis of the finger so as provide a scan which can run from nail to nail.

The effect of the offset between illumination plane and finger axis is to provide a shadowing result along a circumferential line around the finger. This is similar to the shadowing on an axial or longitudinal line along the finger created by the off-normal incidence of the light within the illumination plane.

What has been observed in testing this invention to minimize and maximize shadowing is that there are two phenomenon which reinforce one another to provide a significant image for a wide range of finger surfaces.

The two phenomenon which the device of this invention appears to optimally employ so as to provide meaningful imagery across the wide range of fingers that exist in the population are the phenomenon of shadowing discussed above and the phenomenon of constructive and destructive interference. Although the exact explanation for the manner in which this invention provides observable significantly improved results is not fully understood, it is believed that there is a significant degree of constructive and destructive interference at the image plane by the reflected coherent light such as to substantially enhance the imagery provided by shadowing.

In particular, the coherent light reflected from the ridges constructively interferes to provide bright imagery at the array and the coherent light reflected from the valleys destructively interferes to provide dark imagery at the array of transducers. Notes on Terminology Illumination Plane The illumination plane as used herein refers to a narrow planar like zone which encompasses the linear array of photo-electric transducers. Thus, the plane has thickness and that thickness is substantially determined by the aperture of the diodes that constitute the array. The interrogating light beam is preferably shaped to extend only slightly beyond that plane. By so shaping the interrogating light beam, the light is most efficiently used. That is, the least light is wasted and the least power required As a consequence of this shaping of the interrogating light beam, the reflected modulated light beam bearing fingerprint information also does not extend substantially beyond the thickness of the illumination plane. All light outside the thickness of the illumination plane will be outside of the aperture of the transducers and not contribute to the image formed.

If the interrogating light beam were not shaped to closely conform to this illumination plane, the invention would still operate and there would be a diminution of the intensity of the illumination and thus a reduction of contrast between the light and dark pixels produced by the transducer array. But there would still be an illumination plane; which plane would continue to be defined by the location and aperture width of the transducer array and the optical axis of the imaging lens.

Collimated

The laser diode and focusing lens assembly provide a beam of coherent substantially collimated light. The collimation avoids light scattering and light loss. It is not essential that there be no divergence or convergence of this light beam since some divergence or convergence is inevitable and can be accommodated by the various lenses. Accordingly, the collimated light referred to herein is to a preferred or ideal situation in which the individual rays remains parallel. It should be understood that the invention operates in a practical embodiment with a light beam having some degree of divergence or convergence. Indeed, in a practical embodiment it is not essential that all rays remain unscattered. Some of the rays may cross over one another as long as the bulk of the rays do not cross over one another. Indeed, as a practical matter, to achieve light efficiency by providing an intense light at the finger object, it is useful to have a gradually converging beam. An interrogating light beam of the sort discussed above is essential to achieve the shadowing effect.

Geometric Distortion

The slit of light which illuminates the finger at any one moment and which is defined by the illumination plane is impinging on a surface which curves in two directions. Accordingly, as that slit scans across the finger from nail to nail, the image at the array would change its linear shape unless the plane of the interrogating light beam and the plane of the modulated light beam were coincident. The term geometric distortion is used herein to refer to the change in the linear geometry of the image being interrogated over the course of the scan where there is a departure from coplanarity.

Object Plane

The focusing lens is used to focus the image of the slice of finger being illuminated on the array of transducers. This lens obeys the usual inverse law relationship between image distance and object distance that is determined by the focal length of the lens. The apparatus of this invention is set up so that for the image distance (that is, the distance of the array from the plane of the focusing lens), the object distance determined by that inverse law will be slightly upstream from the surface of the finger being interrogated. Thus, the object plane of the apparatus described herein is not coincident with the surface of the finger. However, the object plane is quite close to the surface of the finger. Depending upon the thickness of the finger in the support structure the object plane may be two to seven millimeters upstream from the finger surface. If the object plane were at the finger surface, there would be little or no contribution to the image at the array from the interference relationship of the coherent light incident on the array. This slight out of focus condition provides the interference enhancement of the image. The shadowing factor is not significantly affected by this out of focus condition.

Reflected Modulated Light Beam

The interrogating light beam 16 is bounced off the finger object as a modulated light beam 22 carrying fingerprint information. This beam 22 includes light that bounces off the finger by specular reflection as well as by diffused or scattered reflection. The use of the term reflected herein is not intended to imply solely mirror-like reflection.

DESCRIPTION OF THE PREFERRED EMBODIMENT

Referring now to the drawings, FIG. 1 illustrates the improved optical finger image processing apparatus of the present invention. The apparatus includes a linear photodiode array 12 which is conventional in construction. One diode array employed has 2,048 charge coupled photodiodes. The diodes are aligned in contact with one another. Accordingly, the shape of the light receiving aperture of the array is in the form of a slit wherein the long dimension of the slit corresponds to the longitudinal direction of the array.

A laser diode 14 is used as a source of an interrogating light beam 16. Laser diode 14 provides a beam of coherent light, which is shaped into a collimated form by lenses. The term "collimated" as used herein refers to an idealized concept and is used to facilitate the discussion of the invention. It should be kept in mind that in a practical case, the light beam may be diverging, parallel or converging and indeed a practical system can tolerate having some of the individual rays cross over one another as long as the amount of scattering is minimal.

The spherical lens assembly 18 and a cylindrical lens 20 in the path of the interrogating light beam 16 shape the light into a narrow slit and concentrate the light so that adequate light intensity is provided. A slightly converging beam 16 provides the best control over the slit of light at the finger F.

Interrogating light beam 16 is modulated by the finger F to provide a reflected light beam 22 containing fingerprint information.

An imaging lens assembly 24 projects the fingerprint image carried by the reflected light beam 22 onto the CCD array 12. The fingerprint image projected onto the array 12 contains light and dark spots indicating fingerprint information. It is preferable that the array 12 be positioned so that the plane of the light receiving aperture of the array 12 be perpendicular to the illumination plane.

A rotatable support 38 provides a mount for the laser 14, the beam forming lenses 18 and 20, the imaging lens 24 as well as the CCD array 12. This support 38 is rotatable about the axis X—X and in use is rotated over an arc of up to 180 degrees. This rotation of the interrogating beam 16 makes possible a full roll image and keeps the angle of incidence of the light beam 16 on the finger F within a range that provides useful modulated information. The axis X—X is the nominal axis of the finger F being interrogated. The support element 38 is mounted for rotational movement on bearings 39.

Coupled to the shaft on which the support element rotates is a rotary position encoder 40. The encoder 40 is conventional and produces a signal each time the support 38 rotates an incremental distance. In the array 12, each of the diodes are about 0.01 mm (about 0.5 mil) on a side. The encoder 40 is calibrated to produce a synchronizing signal each time the support rotates through an arc which displaces the image at the array about 0.01 mm. Simultaneous with the initiation of the scan, the encoder 40 produces a synchronizing signal which is applied to an electronic scanning circuit which is coupled to the CCD array output on the leads 12a. The electronic scanning circuit is conventional in construction and is adapted to serially interrogate each of the CCD elements that comprise the array 12 in response to the synchronizing signal. Thus, the optical scan which is along one axis (perpendicular to the axis X—X) is electronically scanned along the other axis (the line of the array 12) in a periodic fashion that produces a series of signals that constitute the picture elements or pixels of the image being generated.

The interrogating light beam 16 is shaped by the lenses 18 and 20 to provide a long, narrow, planar-like interrogating light beam. The length of the light beam as incident on the finger is about 2.5 cm (one inch) in one embodiment substantially parallel to the axis X—X. The width of the light beam is about 0.1 mm to 0.12 mm at the finger F. This width is along a direction substantially orthogonal to the direction of the axis X—X.

Thus, the light rays are concentrated to provide a narrow slit illumination. The light rays that are within this interrogating slit define a plane that is parallel to but does not intersect the axis X—X. As shown in FIG. 2, there is an offset distance "d" between the illumination plane 42 and the axis X—X. The rotation of the optical system about the axis X—X maintains this parallel relationship and also maintains the distance "d" between the illumination plane and the axis X—X. In the embodiment tested, this offset distance is about 1.525 mm (0.06 inches).

Within the plane 42 of the interrogating beam 16, the incident rays are at an angle to the finger surface line being interrogated. For purposes of illustration, FIG. 1 exaggerates the angle of incidence of the rays in the interrogating beams 16. In one embodiment the incident angle is eleven degrees (11°) in the plane of FIG. 1.

The combined result of the 1.5 mm offset "d" and the 11° angle of incidence within the illumination plane 42 is that shadowing of the valleys occurs in both axes. This shadowing creates a dark valley and bright ridge image at the array 12. The distance "r" from the axis X—X to the line of interrogation of a nominal finger is about 8.7 mm. Thus, the 1.5 mm offset "d" tends to create about as much shadowing along one axis as does the 11° incidence angle in the other axis.

Apparatus 10 does not use a platen. The finger F is held on a finger support 32 and positioned by fingertip positioning element 36. The two supports 32 and 36 are spaced from one another. Thus, a portion of finger F extends beyond the front edge 32f of support 32. Although it is preferable to use support 32, it is possible to practice the invention without such a support if the finger to be scanned is held still in proper position in the path of interrogating beam 16.

The ratio of the distance between finger F and lens 24 and the distance between array 12 and lens 24 determines the minification value of system 10. For example, in one embodiment of the invention, the distance between the finger F and lens 24 is about 13.1 cm (5.16 inches) while the distance between the array 12 and lens 24 is about 8.74 cm (3.44 inches) thereby providing a minification value of 1.5.

That embodiment provides a 0.019 mm (0.75 mils) resolution of the finger object. The array 12 has a 0.013 mm (0.51 mil) center distance between cells. The average ridge to ridge spacing of a finger is about 0.4 mm (15 mils).

FIG. 1 exaggerates the off-normal angle of the incident light beam 16 and reflected light beam 22. In one embodiment, the incident light beam is eleven degrees (11°) off-normal and the optical axis of the lens 24 is four degrees (4°) off normal. It may be noted that a mirror reflection is not presumed and indeed the angle of the axis of the imaging lens 24 in the reflected light beam can be varied.

An embodiment has been tested. It produces an image which has a distinct bright line along the crest of the ridge of the fingerprint and a substantially low level or dark zone between crests. The bright line constitutes perhaps ten to fifteen percent of the ridge to ridge distance and the dark zone constitute the other 85 to 90 percent of that distance. The bright crest line appears to be a result of reinforcement due to constructive interference of the reflected modulated light beam. The dark zone appears to represent a destructive interference of the reflected light. The background slowly varying DC component is sufficiently low relative to the amplitude of the crest line so that it can readily be subtracted out leaving a meaningful and usable image. In addition, the image comes through in substantially clear fashion over any background noise.

What has been found is that this interference result can be achieved only if coherent light is used. The precise mechanisms by which the coherent light provides reinforcement along the crests of the ridges and cancellation over the rest of the image is not completely understood. A test embodiment (without the offset "d") has been checked by being illuminated with a light source which is incoherent, collimated and monochromatic. But that source fails to produce a meaningful, usable image comparable to that produced by the coherent interrogating light beam. The system has also been checked with an optical inspection lamp which provides an interrogating beam that is incoherent, highly collimated but that is not monochromatic. The result is also relatively useless. The conclusion reached is that coherency is an essential feature. Accordingly, it is concluded that the reinforcement along the ridge crests is due to constructive electrical phase interference and the substantial absence of light over the rest of the image is due to destructive electrical phase interference.

The constructive reinforcement that occurs in the light at the crest of the ridges is due to the varying nature of the object involved. FIG. 3 shows, in idealized form, the relationship of ridges to valleys as seen along a plane taken normal to the finger surface. The ridges R are substantially thicker than the valleys V. The ratio between R and V may be four to one or five to one. When the finger object is applied to a platen, the center portion of the ridges are flattened out against the glass platen. The rest of the ridges and the valley zones are spaced back from the surface of the glass platen. Since the image reflected is that at the back surface of the glass platen, the result is an image that has ridge and valley zones which are much more similar in thickness to one another than exists in the actual object as illustrated in FIG. 3. In certain areas of the finger of some individuals, where the pressure of the finger against the platen is great enough, the ridges flatten out sufficiently to close down on the valleys. But normally a good part of the ridges do not even contact the platen surface.

As a practical matter, because the typical valley width is such a small fraction of the ridge to ridge spacing, it becomes necessary that the resolution of the system be at least as fine as about 0.02 mm (0.75 mils) per pixel. This will make sure that the valley width of the population of fingers will be appropriately imaged.

However, in connection with the direct platen-less finger reading of this invention, it may be seen that the variation of optical distance along the ridge zone, is fairly slight relative to the variation in optical distance throughout the valley zone. It is believed that this is at the heart of why, with coherent light, constructive and destructive reinforcement is observed. It is believed that what happens is that points along the ridge surface which are close to one another but which have slightly different focal distances can and do end up as the same point in the image plane. As a consequence, there is constructive reinforcement. This provides substantially enhanced illumination along the center of the crest of the ridge zone in the image plane. Because the ridge surface does indeed have certain irregularities and optical distance variations, the reinforcement may not be uniform throughout the ridge surface and may not even be uniform throughout the crest of the ridge surface. However, it is sufficiently uniform to provide net reinforcement within each pixel along the crest of the resultant image at the resolution involved, which is a resolution of 0.02 mm (0.75 mils) per pixel.

By contrast, the destructive interference which occurs in the light reflected out of the valley areas is a result of the fact that the more substantial and more varying differences in the focal lengths of various points in the valley zones results in electrical phase cancellation and thus a dark zone at the image plane.

It is important that the finger be positioned so that the finger surface being scanned is slightly downstream from the object plane. This condition is necessary to provide the constructive and destructive interference at the array produced by the coherent light. The shadowing effect is not critically affected by being out of focus. The depth of focus of the focusing lens 24 should be great enough to accommodate the small amount of this slight displacement from the object plane. Of course, if the out of focus condition goes past a certain optimum point, then one starts losing information.

The adjustment along the optical axis that should be made is such that the narrowest expected finger has its surface downstream from the object plane by about 2 mm. As a consequence, the fattest expected finger will be downstream from the object plane by 6 or 7 mm. Such dimensions keep the finger object surface sufficiently in focus so that the desired information is not lost and the destructive and constructive interference effect will occur to enhance the shadowing effect. It might be noted that this 2 mm to 7 mm displacement from the object plane is for an object distance of about 13.1 mm from the lens 24.

Alternatively, the arrangement could be such that the fingers are slightly upstream from the object plane. In that case, the dimensions would be set so that the fattest expected finger would be upstream from the object plane by about 2 mm and the thinnest expected fingers should be 6 to 7 mm upstream from the object plane.

The lens 24 should have a reasonable depth of focus to take into account the variety of fingers, the fact that the surface being scanned will vary axially by the difference between the thickness of fingers of different individuals and also by the fact that the individual finger being scanned is not perfectly cylindrical.

This interference effect due to the use of coherent light and the shadowing effect due to the angling and offset of collimated light are reinforcing effects to provide a device that is effective with a wide range of the population.

Presumably any interrogating light beam would provide a reflected light beam in which finger image modulation would exist to some extent. However, that image information would be so swamped out by the background illumination which results from the diffusing and varied nature of the finger object itself that there is no practical way to extract such information from the large and varying base line or pedestal within which it is effectively buried.

The relationships discussed herein have assumed that the finger surface being scanned can be treated as a circular cylinder around the axis X—X. Although the actual surface differs from that ideal concept, it is close enough so that the system as described operates in a practical embodiment to provide a practical result. Any deviations from that ideal still provides results which have fewer distortions or deviations than occur with a system employing a platen.

However, it is essential that the line of the array 12 (a line parallel to the plane of FIG. 1) and the optical axis through imaging lens 24 define a plane that is the same as the plane of the interrogating beam 16. This co-planar feature is the key to the ability to make a rotational scan of a finger surface F which is not a true cylinder. As long as the array lies within that plane, the entire line of the finger that is being illuminated will be received at the array 12.

What is claimed is:

1. An optical finger image processing apparatus comprising:
   finger positioning means to provide an exposed finger surface for a finger positioned therein,
   an optical interrogating and detecting unit for interrogating the surface of a finger held in said positioning means with a coherent light beam having a interrogating zone in the form of a slit to provide a reflected light beam having a modulated light zone in the form of a slit, the plane of the modulated zone and the plane of the interrogating zone being substantially coplanar to define an illumination plane,
   said optical unit including a source of said light beam, a beam forming lens optically upstream from the finger being interrogated, an imaging lens optically downstream from the finger being interrogated, and a linear array of photo-electric transducers optically downstream from said imaging lens, the optical axis defined by said beam forming lens and imaging lens and a line of said linear array of transducers being within and defining said illumination plane, and
   means to rotate said optical interrogating and detecting unit through a predetermined arc about a predetermined axis, said predetermined axis being the nominal central axis of a finger positioned by said finger positioning means, rotation through said arc causing said illumination plane to scan an exposed surface of the finger in said support means,
   said illumination plane being parallel to said predetermined axis during all positions of said rotation.

2. The apparatus of claim 1 wherein said beam forming lens forms the light beam from said source into a predetermined slit light beam, said interrogating zone being contained within said slit light beam.

3. The apparatus of claim 2 wherein:
   said illumination plane and said predetermined axis are spaced from one another by a predetermined offset,
   the light in said illumination plane being incident at a predetermined off-normal angle to the finger surface being illuminated, said off-normal angle being with reference to a plane that is perpendicular to said predetermined axis.

4. The apparatus of claim 3 wherein:
   the image plane defined by said transducers being a principal image plane of said lens for an object plane nominally displaced from the finger object surface being interrogated.

5. The apparatus of claim 4 wherein said object plane is upstream from the finger surface being interrogated 6. The apparatus of claim 2 wherein:
   the image plane defined by said transducers being a principal image plane of said lens for an object plane displaced from the finger object surface being interrogated.

7. The apparatus of claim 6 wherein said object plane is upstream from the finger surface being interrogated.

8. The apparatus of any of claims 2, 3, 6, 4, 7 or 5 wherein said finger support means is adapted to leave a finger supported therein unobstructed over a full roll arc and wherein said means to rotate said optical interrogating and detecting unit causes said interrogating zone to interrogate whatever finger is held in said support means over said full roll.

9. The apparatus of claim 8 wherein the image provided at said array of transducers has a resolution at least as fine as 0.02 mm (0.75 mils) of finger surface per pixel.

10. An optical finger image processing apparatus to provide a fingerprint image of a finger held at a predetermined position therein, the apparatus comprising:
    illumination means to provide a coherent, light beam having an interrogating zone in the form of a slit, said zone being incident on a finger held at said predetermined position, optical focusing means, including a linear array of transducers, optically downstream from the finger to receive a modulated light zone in the form of a slit that is reflected from the finger being interrogated by said interrogating zone, the plane of the modulated zone and the plane of the interrogating zone being substantially coplanar to define an illumination plane, means to rotate said illumination means and said optical focusing means through a predetermined arc about a predetermined axis, said predetermined axis being the nominal central axis of the finger being interrogated, rotation through said arc causing said illumination plane to scan an exposed surface of the finger, said illumination plane being parallel to and offset from said predetermined axis during all positions of said rotation, the light in said illumination plane being incident at a predetermined off-normal angle to the finger surface being interrogated, said off-normal angle being with reference to a plane that is perpendicular to said predetermined axis, the image plane of said transducers being a principal image plane of said optical means for an object plane displaced from the finger object surface being interrogated.

* * * * *